United States Patent [19]

Bellini et al.

[11] 4,391,825
[45] Jul. 5, 1983

[54] N-[[6-(LOWER ALKOXY)-5-(TRIFLUOROMETHYLTHIO)-1-NAPHTHALENYL]THIOXOMETHYL]-N-(LOWER ALKYL)GLYCINES

[75] Inventors: Francesco Bellini, Mount Royal; Kazimir Sestanj, St. Laurent; Leslie G. Humber, Dollard des Ormeaux, all of Canada

[73] Assignee: Ayerst, McKenna & Harrison Inc., Montreal, Canada

[21] Appl. No.: 321,300

[22] Filed: Nov. 13, 1981

[30] Foreign Application Priority Data

Oct. 15, 1981 [CA] Canada ................................ 387991

[51] Int. Cl.³ ................ C07C 153/063; A61K 31/165
[52] U.S. Cl. ..................................... 424/319; 560/10; 562/427
[58] Field of Search ............... 560/10; 562/427; 424/309, 319

[56] References Cited

U.S. PATENT DOCUMENTS 3,489,793 1/1970 Bertelli ............................... 562/450
3,821,383 6/1974 Sestanj et al. ...................... 424/258

OTHER PUBLICATIONS

Allinger, "Organic Chemistry", pp. 532-537, (1971).

D. Dvornik et al., Science, 182, 1146, (1973).
M. J. Peterson et al., Metabolism, 28, (Suppl. 1), 456, (1979).
A. Lawson and C. E. Searle, J. Chem. Soc., 1556, (1957).
Chem. Abstrs., 86, 189582f, (1977).
Chem. Abstr., 70, 11306a, (1969).
Chem. Abstr., 61, 4333f, (1964), for E. Cioranescu et al., Rev. Chim. Acad. Rep. Populaire Roumaine, 7 (2), 755, (1962).

Primary Examiner—Michael L. Shippen
Attorney, Agent, or Firm—Arthur B. Wilfond

[57] ABSTRACT

Aldose reductase inhibitors of the formula

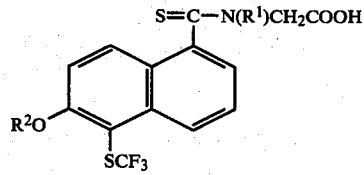

wherein $R^1$ and $R^2$ each is lower alkyl, or a therapeutically acceptable salt thereof with an organic or inorganic base, are useful for treating diabetic complications.

8 Claims, No Drawings

N-[[6-(LOWER ALKOXY)-5-(TRIFLUOROMETHYLTHIO)-1-NAPHTHALENYL]THIOXOMETHYL]-N-(LOWER ALKYL)GLYCINES

RELATED APPLICATIONS

Related hereto are U.S. patent application Ser. No. 321,306, U.S. patent application Ser. No. 321,304 and U.S. patent application Ser. No. 321,303, all filed on the same date as this application.

This application relates to N-[[6-(lower alkoxy)-5-(trifluoromethylthio)-1-naphthalenyl]thioxomethyl]-N-(lower alkyl)glycines, therapeutically acceptable salts thereof, to a process for their preparation, to methods of use, and to pharmaceutical compositions thereof. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964), L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. Other compounds having a similar utility are the thioxo-1H-benz[de]isoquinoline-2(3H)-acetic acid derivatives of K. Sestanj, U.S. patent application Ser. No. 92,397, filed Nov. 8, 1979 and 1H-benz[de]isoquinoline-2(3H)-acetic acid derivatives of K. Sestanj, U.S. patent application Ser. No. 92,604, filed Nov. 8, 1979. (S)-6-Fluoro-2,3-dihydrospiro(4H-1-benzopyran-4,4'-imidazolidine)-2',5'-dione (sorbinil) is still another compound that has received attention because of its aldose reductase inhibiting properties, see M. J. Peterson et al., Metabolism, 28 (Suppl. 1), 456 (1979).

Accordingly, these compounds represent an important new approach for the treatment of diabetes mellitus.

The novel compounds of the present application, represented below by formula I, are effective inhibitors of aldose reductase. These new derivatives are structurally quite different from the above noted aldose reductase inhibitors. Close prior art compounds, on a structural basis, appear to be a group of thioacylaminoacids, e.g. N-phenylthioxomethyl-N-methylglycine, prepared by A. Lawson and C. E. Scarle, J. Chem. Soc., 1556 (1957) as part of a chemical investigation of the chemical properties of such compounds. These last mentioned compounds were prepared by thiobenzoylation of various amino acids with (thiobenzoylthio)acetic acid. An important structural difference between these compounds and the present derivatives is the different type of aromatic group substituted on the thione portion of the thioamide. Thioacylamides also have been reported [see Chem. Abstr., 86, 189582f (1977) for V. I. Cohen et al., Eur. J. Med. Chem., 5, 480 (1976) and Chem. Abstr., 70, 11306a (1969) for von J. Voss and W. Walter, Justus Leibigs Ann. Chem., 716, 209 (1968)]. The structures of the thioacylamides of Cohen et al and Voss et al differ from the structure of the present derivatives by having at least a different type of N-substitution. Another close prior art compound, on a structural basis, is N-[(1-naphthalenyl)-carbonyl]glycine, [see Chem. Abstr., 61, 4333f (1964) for E. Cioranescu et al., Rev. Chim. Acad. Rep. Populaire Roumaine, 7 (2), 755 (1962)].

SUMMARY OF THE INVENTION

The compounds of this invention are represented by formula I

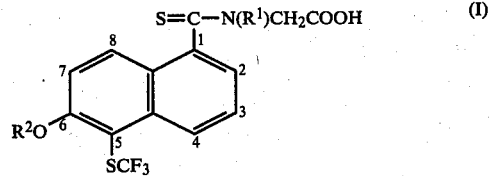

wherein $R^1$ is lower alkyl and $R^2$ is lower alkyl, or a therapeutically acceptable salt thereof with an organic or inorganic base.

A preferred group of the compounds is represented by formula I wherein $R^1$ is methyl and $R^2$ is lower alkyl, or a therapeutically acceptable salt thereof with an organic or inorganic base.

The preferred compound is the compound of formula I wherein $R^1$ is methyl and $R^2$ is methyl, or a therapeutically acceptable salt thereof with an organic or inorganic base.

The compound of formula I can be prepared by a process wherein a corresponding ester of the compound of formula I is hydrolyzed. In a preferred embodiment, the ester is represented by formula II

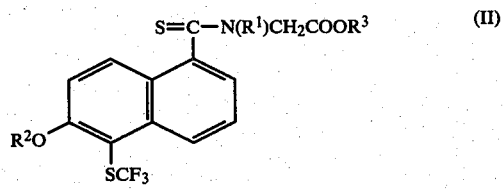

wherein $R^1$ and $R^2$ are as defined herein and $R^3$ is lower alkyl or ar(lower)alkyl.

A method is provided for preventing or relieving diabetes mellitus associated complications in a diabetic mammal by administering to said mammal a prophylactic or alleviating amount of the compound of formula I or therapeutically acceptable salt thereof with an organic or inorganic base. These complications include neuropathy, nephropathy, retinopathy and cataracts.

The compound of formula I, or a therapeutically acceptable salt thereof with an organic or inorganic base, when admixed with a pharmaceutically acceptable carrier, forms a pharmaceutical composition which can be used according to the preceding method.

DETAILED DESCRIPTION OF THE INVENTION

The compounds of this invention, represented by formula I, can exist in rotameric forms. More explicitly, mesomerism imparts a partial double bond character to the carbon-nitrogen bond of the thioamide group. This partial double bond character leads to restricted rotation about the carbon nitrogen bond giving rise to cis and trans rotamers, the restricted rotation being augmented by the bulkiness of neighboring groups. Interconversion of the rotamers is possible and is dependent on the physical environment. As evidenced by its physical properties, the thermodynamically more stable rotamer exists exclusively in the crystalline state of the compound and is the predominant isomer present in equilabrated solutions. Furthermore, the more stable rotamer is the more pharmacologically active. The less stable rotamer can be separated from the more stable rotamer by high performance liquid chromatography or by thin layer chromatography. The rotameric forms are included within the scope of this invention. For brevity, the compounds of this invention, including their rotameric forms, will be referred to herein as compounds of formula I.

The term "lower alkyl" as used herein means a straight chain alkyl radical containing from one to four carbon atoms or a branched chain alkyl radical containing three or four carbon atoms and includes methyl, ethyl, propyl, 1-methylethyl, butyl, 2-methylpropyl and 1,1-dimethylethyl. Preferred lower alkyl radicals contain from one to three carbon atoms.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexanoxy.

The term "halo" as used herein means chloro, bromo and iodo.

The term "ar" as used mean an aromatic radical containing at least one benzene ring. The preferred aromatic radical is phenyl.

The term "organic proton acceptor" as used herein means the organic bases or amines, for instance, triethylamine, pyridine, N-ethylmorpholine, 1,5-diazabicyclo[4.3.0]non-5-ene and the like.

The compounds of formula I form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, and alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethyl-piperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any access can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular hose under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 0.1 mg to about 100 mg per kilo of body weight per day, although aforementioned variations will occur. However, a dosage level that is in the range of from about 0.5 mg to about 30 mg per kilo of body weight per day is most satisfactory.

Unit dosage forms such as capsules, tablets, pills and the like may contain from about 5.0 mg to about 250 mg of the active ingredients of this invention, preferably with a significant quantity of a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, for example, sodium N-[[5-(trifluoromethyl)-6-methoxy-1-naphthalenyl]thioxomethyl]-N-methylglycinate, and may advantageously contain glycerol and ethyl alcohol as solvents or preservatives.

The compound of formula I, or a therapeutically acceptable salt thereof, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S.A., 1980. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

For example, when N-[[6-methoxy-5-(trifluoromethylthio)-1-naphthalenyl]thioxomethyl]-N-methylglycine, the compound of formula I wherein $R^1$ and $R^2$ are methyl, was evaluated in the above in vitro test, the aldose reductase from the bovine lens was inhibited 94,73 and 9 percent by compound concentrations of $1\times10^{-6}$, $1\times10^{-7}$ and $1\times10^{-8}$ M, respectively.

The aldose reductase inhibiting property of the compounds of this invention and the utilization of the compounds in preventing, diminishing and alleviating diabetic complications are demonstrable in experiments using galactosemic rats, see Dvornik et al., cited above. An example of such an experiment is exemplified hereinbelow after the listing of the following general comments pertaining to these experiments:

(a) Four or more groups of six male rats, 50–70 g, Spraque-Dawley strain, were used. The first group, the control group, was fed a mixture of laboratory chow (rodent laboratory chow, Purina) and glucose at 20% (W/W %) concentration. The untreated galactosemic group was fed a similar diet in which galactose is substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and could be kept up to two weeks before being analyzed for dulcitol.

(c) The polyol determination was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding rat tissue to obtain the amount of polyol accumulated].

When N-[[6-methoxy-5-(trifluoromethylthio)-1-naphthalenyl]thioxomethyl]-N-methylglycine was evaluated in the above in vivo test, the results appearing in the following table were obtained. In the table, the figures under L, N and D represent the percentage decrease of dulcitol accumulation in the tissues of the lens, sciatic nerve and diaphragm, respectively, for treated rats as compared to untreated rats.

| Dose mg/kg/day | L | N | D |
|---|---|---|---|
| 20.5 | 20 | 96 | 87 |
| 9.1 | NS* | 55 | 83 |
| 4.4 | NS | 29 | 83 |

*Not Significant

PROCESS

As noted previously, the compounds of formula I are prepared preferably by hydrolyzing the corresponding ester of formula II wherein $R^1$, $R^2$ and $R^3$ are as defined herein.

More explicitly, the ester of formula II is hydrolyzed with a hydrolyzing agent to give the corresponding product of formula I in which $R^1$ and $R^2$ are as defined herein. Generally speaking, the hydrolysis is performed most conveniently by employing a base as the hydrolyzing agent in the presence of sufficient water. However, it should be understood that the manner of hydrolysis for the process of this invention is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1969, pp. 615–617), also are applicable. Hydrolysis under acidic conditions is preferred when the ester is a ter-butyl ester.

For basic hydrolysis, a preferred embodiment involves subjecting the ester to the action of a strong base, for example, sodium hydroxide or potassium hydroxide, in the presence of sufficient water to effect hydrolysis of the ester. The hydrolysis is performed using a suitable solvent, for example, methanol, ethanol or 2-methoxyethanol. The reaction mixture is maintained at a temperature of from about 25° to 100° C. or at the reflux temperature of the solvent employed until hydrolysis occurs. Usually from 10 minutes to six hours is sufficient for this hydrolysis. The reaction mixture is then rendered acidic with an acid, for example, acetic acid, hydrochloric acid or sulfuric acid, to release the free acid of formula I.

The requisite ester of formula II for the preceding hydrolysis step can be prepared by a process which is illustrated by the following reaction scheme wherein $R^1$ and $R^2$ each is lower alkyl, $R^3$ is lower alkyl or ar(-lower)alkyl, $R^4$ is lower alkyl and X is halo.

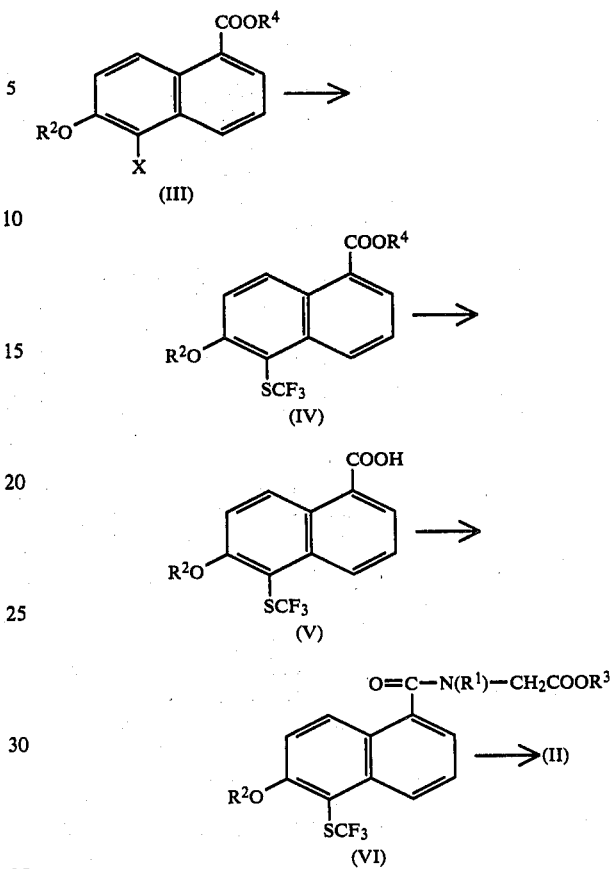

With reference to the reaction scheme, the ester of formula III wherein $R^2$ and $R^4$ each is lower alkyl and X is halo can be prepared by known methods. For example, see "Elesevier's Encyclopedia of Organic Chemistry", F. Radt, Ed., Series III, Vol. 12B, Elsevier Publishing Co., Amsterdam, 1953, pp 3965–4473.

The ester of formula III wherein $R^2$ and $R^4$ each is lower alkyl and X is halo is reacted with trifluoromethylthio copper to give a second ester represented by formula IV wherein $R^2$ and $R^4$ each is lower alkyl. Practical and convenient conditions for effecting this conversion include reacting the ester of formula III with one to two molar equivalents of trifluoromethylthio copper at 80°–120° C. for two to six hours in an inert organic solvent, for instance, dimethylformamide, m-xylene or toluene.

Thereafter, the ester of formula IV is hydrolysed to give the corresponding naphthalenecarboxylic acid of formula V wherein $R^2$ is lower alkyl. Suitable conditions for this hydrolysis are the same as those described previously for the hydrolysis of the ester of formula II to obtain the compound of formula I.

The corresponding naphthalenecarboxylic acid of formula V wherein $R^2$ is lower alkyl is coupled with an amino acid ester of the formula $NH(R^1)$—$CH_2COOR^3$ where $R^1$ is lower alkyl and $R^3$ is lower alkyl or ar(lower)alkyl to give the amidoester of formula VI wherein $R^1$, $R^2$ and $R^3$ are as defined herein. The coupling is done preferably by the "carboxyl activation" coupling procedure. Descriptions of carboxyl-activating groups are found in general textbooks of peptide chemistry; for example K. D. Kopple, "Peptides and Amino Acids", W. A. Benjamin, Inc., New York, 1966, pp. 45–51 and E. Schröder and K. Lübke, "The Peptides"; Vol. 1, Academic Press, New York, 1965, pp. 77–128. Examples of the activated form of the terminal carboxyl are the acid chloride, acid bromide, anhydride, azide, activated ester, or O-acyl urea of a dialkylcarbodiimide. Preferred activated forms of the carboxyl are the acid chloride or the 1-benzotriazolyl, 2,4,5-trichlorophenyl or succinimido activated esters.

Finally, the amidoester of formula VI, the product of the above described coupling reaction, is reacted under anhydrous conditions with about two to five molar equivalents of phosphorus pentasulfide in an inert solvent, e.g. xylene or toluene, to give the desired, corresponding thioxoester of formula II. This reaction is performed conveniently at temperatures ranging from 80 to about 150° C. and for a duration ranging from 20 minutes to four hours. Preferably, the reaction is performed in the presence of an organic proton acceptor; for instance, N-ethyl morpholine, triethylamine or pyridine.

The following examples illustrate further this invention.

EXAMPLE 1

5-Iodo-6-methoxy-1-naphthalenecarboxylic Acid Methyl Ester (III, $R^2$ and $R^4$=CH$_3$ and X=I)

Iodine (7.08 g) and iodic acid (2.78 g) were added to a stirred solution of 6-methoxy-1-naphthalenecarboxylic acid methyl ester [15 g, 69.4 mmoles, described by C. C. Price et al., J. Amer. Chem. Soc., 69, 2261 (1947)] in 80% acetic acid (110 ml) and 98% sulfuric acid (0.97 ml). The solution was heated at 50° C. for 5 hr, cooled and poured into water (100 ml). After the addition of sodium bisulfite to destroy the unreacted iodine, the precipitate was collected, washed with water and recrystallized from ethanol to afford the title compound; mp 98°–99° C.; NMR (CDCl$_3$) δ 3.95 (s, 3H), 4.00 (s, 3H), 8.00 (m, 5H).

EXAMPLE 2

6-Methoxy-5-(trifluoromethylthio)-1-naphthalenecarboxylic Acid Methyl Ester (IV, $R^2$ and $R^4$=CH$_3$)

An intimate mixture of copper dust (1.84 g, 29 mmoles) and Hg (SF$_3$)$_2$ [3.27 g, 8 mmoles, prepared according to the method of E. H. Man et al., J. Amer. Chem. Soc., 81, 3575 (1959)] was heated between 80° to 100° C. for 2.5 hr. Thereafter, the temperature was increased to 150° C. for 30 min. The mixture, containing CuSCF$_3$, was cooled to room temperature (ca. 22° to 24° C.). A solution of 5-iodo-6-methoxy-1-naphthalenecarboxylic acid methyl ester (1.87 g, 5.4 mmoles) in distilled dimethylformamide (DMF, 10 ml) was added to the mixture. The resulting mixture was stirred at 110° to B 120° C. for 3 hr, and then at room temperature for 18 hr. The mixture was poured into water. The diluted mixture was extracted with diethyl ether (3 x). The extract was washed with water, dried (MgSO$_4$) and evaporated to dryness to give the title compound (1.7 g) as a solid residue; mp 93°–94° C.; NMR (CDCl$_3$) δ 3.90 (s, 3H), 4.00 (s, 3H), 7.00–9.20 (m, 5H).

EXAMPLE 3

6-Methoxy-5-(trifluoromethylthio)-1-naphthalenecarboxylic Acid (V, $R^2$=CH$_3$)

Aqueous NaOH solution (1 N, 15.5 ml) was added to a solution of 6-methoxy-5-(trifluoromethylthio)-1-naphthalenecarboxylic acid methyl ester (2.45 g, 7.7 mmoles) in 2-methoxyethanol (60 ml). The resulting solution was stirred at room temperature for 24 hr, cooled in an ice-bath, made acidic (pH=3) by the addition of 1 N aqueous HCl and diluted with water. The resulting solid was collected, washed with water and recrystallized from ethanol to give the title compound (1.7 g); mp 204°–205° C.; NMR (DMSO-d$_6$) δ 4.00 (s, 3H), 8.20 (m, 5H), 10.30 (broad, 1H).

EXAMPLE 4

N-[[6-Methoxy-5-(trifluoromethylthio)-1-naphthalenyl]carbonyl]-N-methylglycine Methyl Ester (VI, $R^1$, $R^2$ and $R^3$=CH$_3$)

Procedure A:

N,N'-Dicyclohexylcarbodiimide (1.39 g, 6.7 mmoles) was added to a solution of 6-methoxy-5-(trifluoromethylthio)-1-naphthalenecarboxylic acid (1.7 g, 5.6 mmoles) and 1-hydroxybenzotriazole (1.5 g, 11.1 mmoles) in distilled DMF (10 ml). The mixture was stirred at room temperature for one hr. A solution of N-methylglycine methyl ester hydrochloride (1.57 g, 11.2 mmoles) in distilled DMF (10 ml) containing N-ethylmorpholine (1.44 ml) was added to the mixture. The mixture was stirred at 24° C. for 18 hr. Thereafter, the mixture was filtered and the filtrate was concentrated under reduced pressure. The residue was dissolved in ethyl acetate. The solution was washed successively with 1 N aqueous HCl, water, a saturated aqueous solution of NaHCO$_3$, water and brine, dried (MgSO$_4$) and concentrated to dryness under reduced pressure to give 2.0 g of the title compound as an oil; NMR (CDCl$_3$) δ 3.00 (s, 3H), 3.75 (s, 3H), 4.00 (s, 3H), 4.35 and 4.5 (d, 2H), 7.0–8.5 (m, 5H).

Procedure B:

A catalytic amount (5 drops) of dry DMF was added to a suspension of 6-methoxy-5-(trifluoromethylthio)-1-naphthalenecarboxylic acid (10 g, 40 mmoles) in thionyl chloride (100 ml). The suspension was heated cautiously to reflux (caution: a vigorous reaction can occur). The mixture was refluxed for 20 min. The mixture was evaporated to dryness. Toluene was added to the solid residue and the mixture was evaporated to dryness. The residue was dissolved in pyridine (100 ml). The solution was cooled in an ice bath. Dry N-methylglycine methyl ester hydrochloride (11.1 g, 79.6 mmoles) was added portion-wise to the cooled solution. The mixture was extracted with ethyl acetate (3 × 150 ml). The combined extracts were washed with 1 N aqueous HCl solution, a saturated aqueous solution of NaHCO$_3$ and brine. After drying over MgSO$_4$, the extract was treated with charcoal, filtered and evaporated to give a product identical to that obtained by procedure A of this example.

EXAMPLE 5

N-[[6-Methoxy-5-(trifluoromethylthio)-1-naphthalenyl]thioxomethyl]-N-methylglycine Methyl Ester (II, $R^1$, $R^2$ and $R^3$=CH$_3$)

N-[[6-Methoxy-5-(trifluoromethylthio)-1-naphthalenyl]carbonyl]-N-methylglycine methyl ester (2.0 g, 5.4 mmoles) was dissolved in dry pyridine (40 ml). Phosphorus pentasulfide (2.37 g, 10.7 mmoles) was added to the pyridine solution. The mixture was heated at refluxed for 4 hr and then poured into warm water at 50° to 80° C. (caution: evolution of copious quantities of H$_2$S). The mixture was extracted with ethyl acetate. The extract was washed successively with 3 N aqueous HCl, water, a saturated aqueous solution of NaHCO$_3$, water and brine, dried (MgSO$_4$) and concentrated to dryness. The residue was recrystallized from ethanol-water to give 1.6 g of the title compound; mp 121°–123° C.; NMR (CDCl$_3$) δ 3.00 (s, 3H), 3.75 (s, 3H), 4.00 (s, 3H), 4.35 and 4.5 (d, 2H), 7.0–8.5 (m, 5H).

EXAMPLE 6

N-[[6-Methoxy-5-(trifluoromethylthio)-1-naphthalenyl]thioxomethyl]-N-methylglycine (I, R$^1$ and R$^2$=CH$_3$)

Aqueous NaOH (3.41 mL, 2 N) was added to a solution of N-[[6-methoxy-5-(trifluoromethylthio)-1-naphthalenyl]thioxomethyl]-N-methylglycine methyl ester (1.375 g, 3.4 mmoles) in 2-methoxyethanol (20 ml). The solution was stirred at 20°–22° C. for 4 hr. Water was added and the cloudy mixture was extracted with ethyl acetate. The aqueous layer was made acidic (pH=3) with 1 N aqueous HCl and extracted with ethyl acetate. The latter extract was washed successively with water and brine, dried (MgSO$_4$) and concentrated under reduced pressure. The residue was crystallized from chloroform-hexane to give the title compound (672 mg); mp 168°–169° C.; NMR (DMSO-d$_6$) δ 3.0 (s, 3H), 4.0 (s, 3H), 4.6 and 5.2 (d, J=16.5 Hz, 2H), 7.7 (m, 5H); ir (white mineral oil) 2900, 1720, 1465 cm$^{-1}$; uvλmax (MeOH) 342 nm (ε4970), 334 (4800), 230 (46,800).

We claim:

1. A compound of formula I

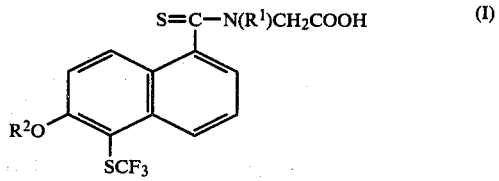

wherein R$^1$ and R$^2$ each is lower alkyl, or a therapeutically acceptable salt thereof with an organic or inorganic base.

2. The compound of claim 1 wherein R$^1$ is methyl, or a therapeutically acceptable salt thereof with an organic or inorganic base.

3. The compound of claim 1 wherein R$^1$ and R$^2$ each is methyl, or a therapeutically acceptable salt thereof with an organic or inorganic base.

4. A pharmaceutical composition for preventing or relieving diabetic complications in a diabetic mammal, which comprises a compound of claim 1, or a therapeutically acceptable salt thereof with an organic or inorganic base, and a pharmaceutically acceptable carrier.

5. A method of preventing or relieving diabetic complications in a diabetic mammal, which comprises administering to said mammal an alleviating or prophylactic amount of a compound of claim 1, or a therapeutically acceptable salt thereof with an organic or inorganic base.

6. The method of claim 5 wherein the diabetic complications are selected for neuropathy, nephropathy, retinopathy and cataracts.

7. N-[[6-(Lower alkoxy)-5-(trifluoromethylthio)-1-naphthalenyl]-thioxomethyl]-N-methylglycine lower alkyl ester.

8. The compound of claim 7 which is N-[[6-methoxy-5-(trifluoromethylthio)-1-naphthalenyl]thioxomethyl]-N-methylglycine methyl ester.

* * * * *